US012564306B2

(12) United States Patent
Shirazian et al.

(10) Patent No.: US 12,564,306 B2
(45) Date of Patent: Mar. 3, 2026

(54) SYSTEMS AND METHODS FOR DEPTH-BASED MEASUREMENT IN A THREE-DIMENSIONAL VIEW

(71) Applicant: INTUITIVE SURGICAL OPERATIONS, INC., Sunnyvale, CA (US)

(72) Inventors: Pourya Shirazian, Menlo Park, CA (US); Daniel Proksch, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 120 days.

(21) Appl. No.: 18/294,975

(22) PCT Filed: Aug. 9, 2022

(86) PCT No.: PCT/US2022/039784
§ 371 (c)(1),
(2) Date: Feb. 2, 2024

(87) PCT Pub. No.: WO2023/018684
PCT Pub. Date: Feb. 16, 2023

(65) Prior Publication Data
US 2024/0341568 A1     Oct. 17, 2024

Related U.S. Application Data

(60) Provisional application No. 63/310,465, filed on Feb. 15, 2022, provisional application No. 63/231,686, filed on Aug. 10, 2021.

(51) Int. Cl.
*A61B 1/00*        (2006.01)
*G06T 15/20*       (2011.01)
(Continued)

(52) U.S. Cl.
CPC ........ *A61B 1/00009* (2013.01); *A61B 1/0005* (2013.01); *A61B 1/00057* (2013.01);
(Continued)

(58) Field of Classification Search
None
See application file for complete search history.

(56) References Cited

U.S. PATENT DOCUMENTS 4,989,083 A    1/1991  Eino
9,547,940 B1   1/2017  Sun et al.
(Continued)

FOREIGN PATENT DOCUMENTS

WO        WO-9610949 A1      4/1996

OTHER PUBLICATIONS

International Preliminary Report on Patentability for Application No. PCT/US2022/039784, mailed Feb. 22, 2024, 07 pages.
International Search Report and Written Opinion for Application No. PCT/US2022/039784, mailed Dec. 2, 2022, 13 pages.
(Continued)

*Primary Examiner* — Frank S Chen
(74) *Attorney, Agent, or Firm* — Haynes & Boone, LLP.

(57) ABSTRACT

A system may comprise a processor and a memory having computer readable instructions stored thereon. The computer readable instructions, when executed by the processor, cause the system to receive endoscope calibration data, generate a virtual camera based on the calibration data, generate an endoscopic image, receive first and second marked points in the endoscopic image, and determine if a three-dimensional surface model has been generated. If a surface model has been generated, a perturbation in the virtual camera is generated. A curvilinear segment on the surface model may be generated between the first and second marked points and a mixed reality image, including the curvilinear segment and the endoscopic image, may be generated.

20 Claims, 8 Drawing Sheets

(51) Int. Cl.
   *G06T 17/20*       (2006.01)
   *G06T 19/00*       (2011.01)
(52) U.S. Cl.
   CPC .............. *G06T 15/20* (2013.01); *G06T 17/20*
         (2013.01); *G06T 19/006* (2013.01); *G06T*
         *2210/41* (2013.01)

(56)            References Cited

U.S. PATENT DOCUMENTS

2002/0077544 A1 *   6/2002   Shahidi .................. A61B 34/20
                                                      606/130
2003/0018235 A1     1/2003   Chen et al.

OTHER PUBLICATIONS

Sielhorst T., et al., "Advanced Medical Displays: A Literature Review of Augmented Reality," Journal of Display Technology, IEEE SErvice Center, New York, NY, US, vol. 4, No. 4, Dec. 1, 2008, pp. 451-467.
Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.
Weersink R A . . . , "Image Fusion and Visualization," Bioengineering for Surgery, Jan. 1, 2016, Elsevier, NL, Chapter 3, pp. 29-58.
Wengert C., et al., "Endoscopic Navigation for Minimally Invasive Suturing," Oct. 29, 2007, 18th International Conference, Austin, TX, USA, Sep. 24-27, 2015; Lecture Notes in Computer Science; Lect.Notes Computer], Springer, Berlin, Heidelberg, pp. 620-627.

* cited by examiner

SYSTEMS AND METHODS FOR DEPTH-BASED MEASUREMENT IN A THREE-DIMENSIONAL VIEW

CROSS-REFERENCED APPLICATIONS

This application is the U.S. national phase of International Application No. PCT/US2022/039784, filed Aug. 9, 2022, which designated the U.S. and claims priority to and the benefit of U.S. Provisional Application No. 63/310,465, filed Feb. 15, 2022, and U.S. Provisional Application No. 63/231, 686, filed Aug. 10, 2021, both entitled "Systems and Methods for Depth-Based Measurement in a Three-Dimensional View," all of which are incorporated by reference herein in their entirety.

FIELD

The present disclosure is directed to systems and methods for displaying and measuring a surface traversing line between points in a three-dimensional image.

BACKGROUND

Minimally invasive medical techniques are intended to reduce the amount of tissue that is damaged during diagnostic or surgical procedures, thereby reducing patient recovery time, discomfort, and harmful side effects. Such minimally invasive techniques may be performed through one or more surgical incisions or through natural orifices in a patient anatomy. Through these incisions or natural orifices, clinicians may insert minimally invasive medical instruments, including endoscopic imaging systems to capture images of tissue within the patient anatomy. The endoscopic imaging systems may be three-dimensional imaging systems that provide a three-dimensional video image of the tissue. Systems and methods for accurately measuring and displaying three-dimensional surface traversing lines or shapes may aid in performing some minimally invasive procedures.

SUMMARY

Examples of the invention are summarized by the claims that follow the description. Consistent with some examples, a system may comprise a processor and a memory having computer readable instructions stored thereon. The computer readable instructions, when executed by the processor, cause the system to receive endoscope calibration data, generate a virtual camera based on the calibration data, generate an endoscopic image, receive first and second marked points in the endoscopic image, and determine if a three-dimensional surface model has been generated. If a surface model has been generated, a perturbation in the virtual camera is generated. A curvilinear segment on the surface model may be generated between the first and second marked points and a mixed reality image, including the curvilinear segment and the endoscopic image, may be generated.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Figure 1:
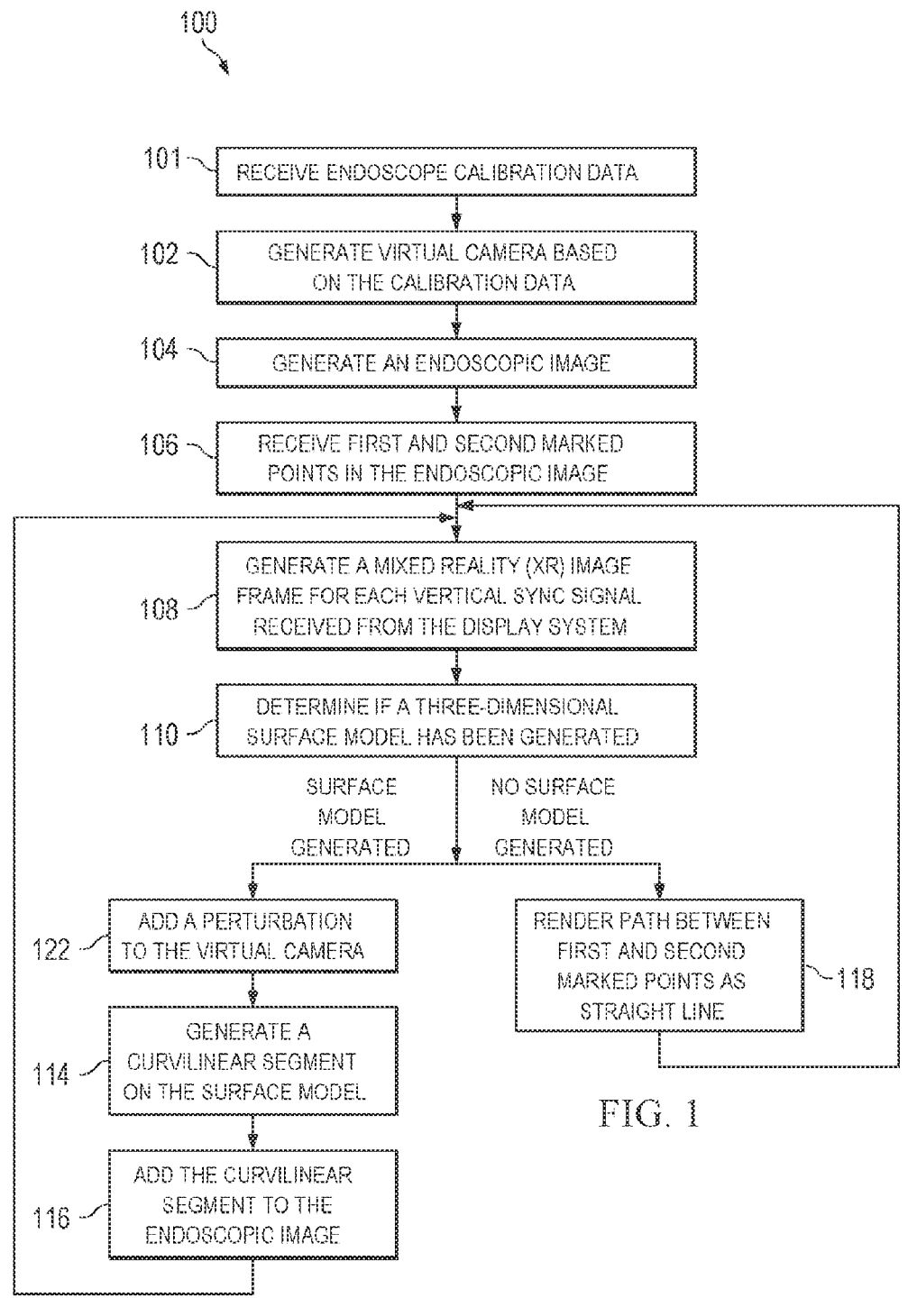
FIG. 1 is a flowchart illustrating a method for generating a mixed-reality image, according to some embodiments.

Embodiments of the present disclosure and their advantages are best understood by referring to the detailed description that follows. It should be appreciated that like reference numerals are used to identify like elements illustrated in one or more of the figures for purposes of illustrating but not limiting embodiments of the present disclosure.

DETAILED DESCRIPTION

A three-dimensional surface model of tissue may be used to generate a curvilinear segment or "flexible ruler" between two identified points on the surface of the tissue in an endoscopic image. A mixed-reality image may be generated including the live endoscopic image and the curvilinear segment. Existing measurement tools and techniques may not capture surface slopes of an anatomic area from multiple viewpoints. As described in detail below, generating a virtual camera and changing the viewpoint of the virtual camera to a slightly different angle from the endoscopic camera may allow the anatomic area to be viewed from another viewpoint. Thus, the virtual camera allows surface slopes not visible in a single frame of the endoscopic view to become visible.

FIG. 1 is a flowchart illustrating a method 100 for generating a mixed-reality image, according to some embodiments. The method 100 is illustrated as a set of operations or processes. The processes illustrated in FIG. 1 may be performed in a different order than the order shown in FIG. 1, and one or more of the illustrated processes might not be performed in some embodiments of method 100. Additionally, one or more processes that are not expressly illustrated in FIG. 1 may be included before, after, in between, or as part of the illustrated processes. In some embodiments, one or more of the processes of method 100 may be implemented, at least in part, in the form of executable code stored on non-transitory, tangible, machine-readable media that when run by one or more processors (e.g., the processors of a control system) may cause the one or more processors to perform one or more of the processes.

Figure 7:
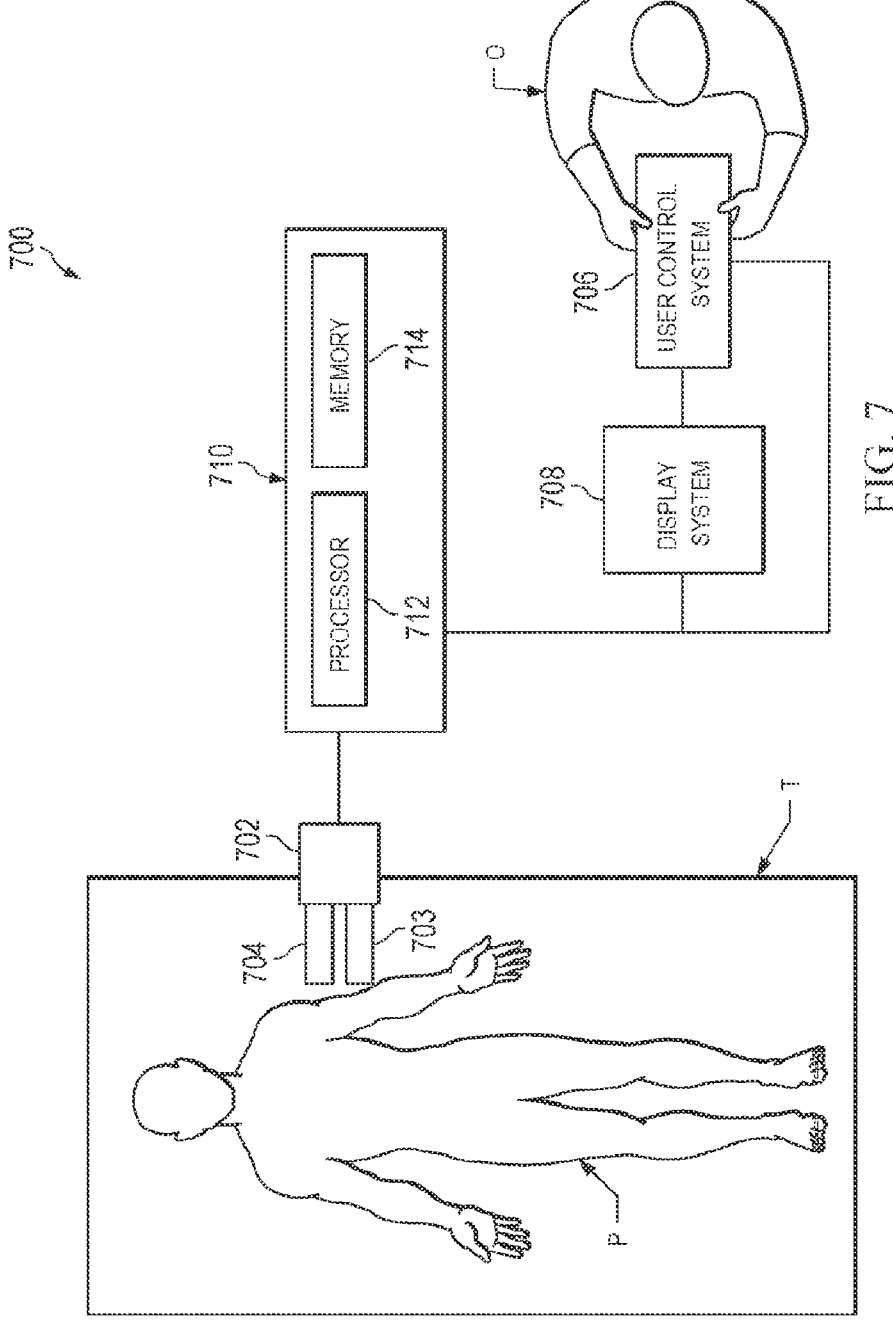
FIG. 7 is a simplified diagram of a robotically-assisted medical system according to some embodiments.

At a process 101, endoscope calibration data is received. The endoscope calibration data may be received from an endoscopic imaging system positioned within a patient anatomy. The received endoscope calibration data may include intrinsic parameters of the endoscopic imaging system, including focal length, principal point, and lens distortion, and/or extrinsic parameters of the endoscopic imaging system, including offset to a world coordinate system and/or other imaging systems or position tracking sensors. The endoscopic imaging system may be a three-dimensional imaging system that generates stereoscopic video or still images. The endoscopic imaging system may be a component of a robotically-assisted medical system. For example, the endoscopic imaging system may include the image capturing device 704 of medical system 700 as shown in FIG. 7. From the stereoscopic images, two dimensional features and a depth map may be determined.

At a process 102, a virtual camera for generating a virtual camera image may be generated based on the intrinsic and extrinsic parameters of the endoscope calibration data. The virtual camera may mimic the behavior of the endoscope (e.g. image capturing device 704), allowing an area within the patient anatomy (e.g., an interventional area or a surgical environment) to be viewed from camera angles or positions different from the position and/or orientation of the live endoscopic view from the endoscope (e.g., image capturing device 704) physically positioned within the patient anatomy. The virtual camera may have the same calibration parameters as the endoscope.

At a process 104, an endoscopic image may be generated from endoscopic image data generated by the endoscopic imaging system (e.g., image capturing device 704). The endoscopic image may be a three-dimensional image generated from a live three-dimensional video of the surgical environment captured by the endoscopic imaging system. The endoscopic image may be displayed on a display system of a robotically-assisted medical system. For example, the endoscopic image may be displayed on the display system 708 of the robotically-assisted medical system 700. While viewing the endoscopic image, the viewer (e.g. operator O) may want to determine distances or surface areas across anatomical surfaces between structures or points visible in the three-dimensional endoscopic image. For example, the operator may want to determine a correct size of surface repair mesh or a length of suture material that may be needed. In some examples, the operator may want to measure the three-dimensional length or surface area of a pathology such as a hernia that is indicated by a bulging tissue, a tumor, or a wound that traverses a visible anatomic surface.

Figure 2:
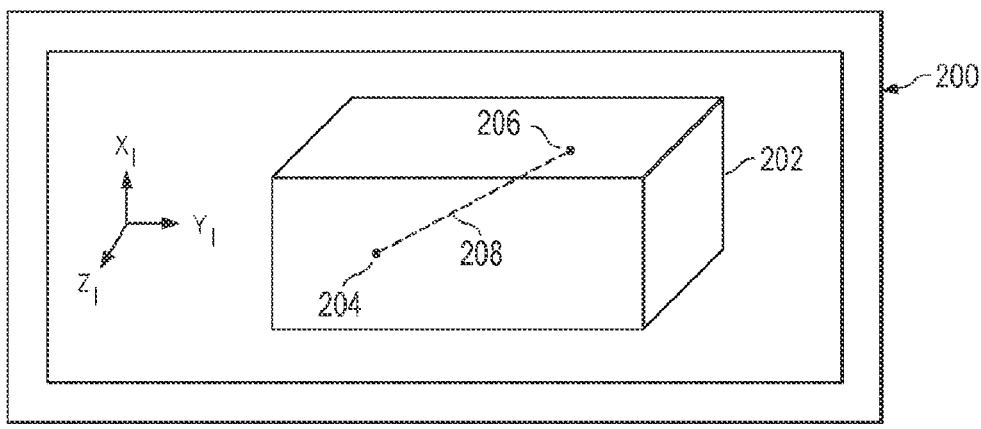
FIG. 2 illustrates an image of marked points on a portion of tissue, according to some embodiments.

To measure a surface traversing line between structures in a three-dimensional image, points visible on the anatomic surface may be marked. At a process 106, first and second marked points are received in the endoscopic image. For example, a clinician may engage a user input device to generate points on the endoscopic image. With reference to the robotically-assisted medical system 700 of FIG. 7, the operator O may operate one or more input devices of the control system 706 to position markers on the endoscopic image. For example, movement of the input devices may correspond to movement of a cursor visible on the endoscopic image visible on the display system 708. The cursor may be positioned at a location on the image and a marker may be placed at the location by an input at the user input device (e.g., grip gesture, a pressed button). For example, FIG. 2 illustrates tissue marking on a portion of a tissue 202 in a three-dimensional endoscopic image 200. The endoscopic image may have an image coordinate frame $X_I$, $Y_I$, $Z_I$. An operator may generate a first marked point 204 and a second marked point 206 on the surface of the tissue 202.

The operator may generate the marked points 204, 206 with a user input device (e.g., user input device of control system 706 of FIG. 7) The user input device, in response to an operator input, may manipulate a two-dimensional cursor in X-Y dimensions. Based on the depth map determined from the three-dimensional endoscopic image, the Z dimension (distance from the distal end of the endoscope) may be determined for each of the marked points 204, 206. In some examples, when measuring long distances in the surgical environment, a clinician may place the first marked point and then pan the endoscopic camera to be able to view and place the second marked point. The first marked point may not be visible to the endoscopic camera when the second marked point is placed.

At a process 108, a mixed reality (XR) image frame may be generated for each vertical synchronization signal received from the display system. For example, a mixed reality frame rate may be synchronized with the refresh rate of the display system 708 of the robotically-assisted medical system 700. The mixed reality image may include the marked points, annotations, or other operator or system generated augmentations to the endoscopic image. FIG. 2 illustrates the mixed reality image frame 200 with the annotated dots indicating the first and second marked points 204, 206.

Figure 3A:
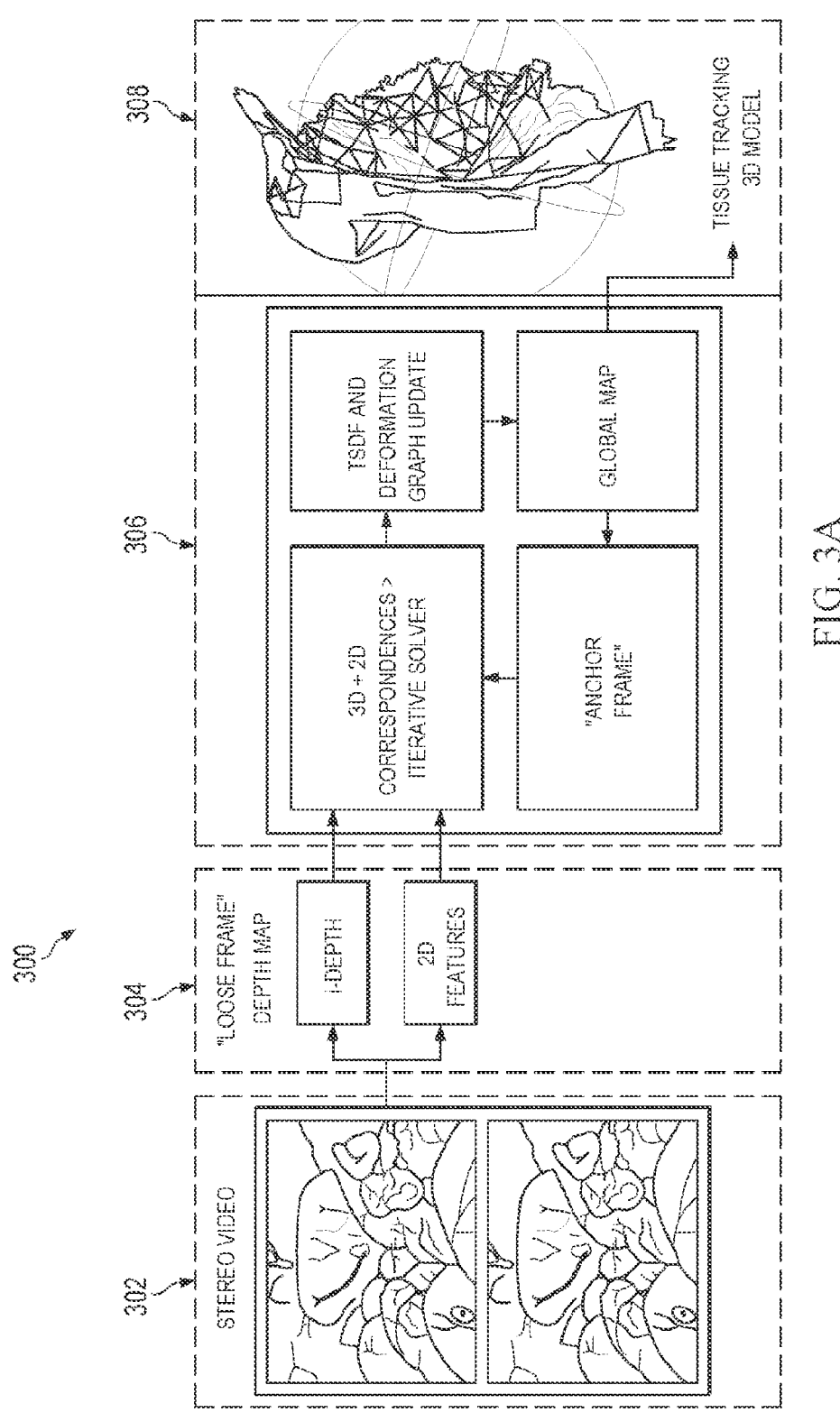
FIG. 3A is a schematic illustration of a process for generating a three-dimensional model using simultaneous localization and mapping, according to some embodiments.
Figure 3B:
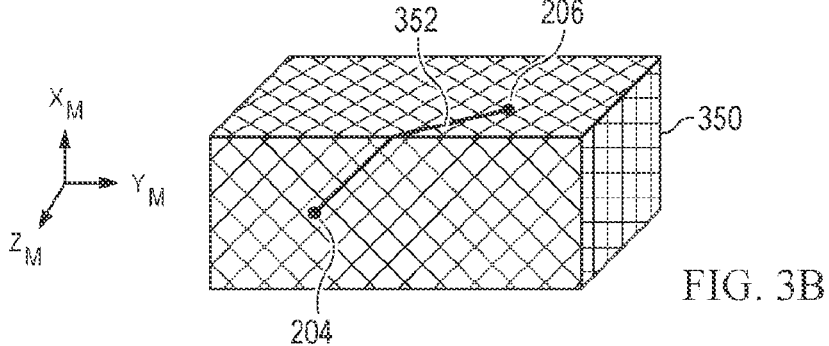
FIG. 3B illustrates a tissue model, according to some embodiments.

At a process 110, a determination is made as to whether a three-dimensional surface model has been generated. In some examples, a three-dimensional surface model may be generated with a simultaneous localization and mapping technique (SLAM). FIG. 3A illustrates a process for generating a three-dimensional mesh surface model using a SLAM technique. At a process 302 stereoscopic video is received from the endoscopic imaging system (e.g., image capturing device 704). At a process 304, loose frame information including two-dimensional features (e.g., X-Y dimensions) and a depth map (Z-dimension and distance from distal end of endoscope) may be determined for each frame of the stereoscopic video. In some examples the displayed image may have a 1280×1024 pixel resolution with a depth map in the same resolution. At a process 306 a SLAM process may be performed using the two-dimensional features and the depth map. The SLAM process may be a recursive process including creating three-dimensional and two-dimensional correspondences with an iterative solver, updating a truncated signed distance function (TSDF) and deformation graph, generating a global map, and generating an anchor frame. At a process 308 a three-dimensional tissue tracking model may be generated. In some examples, the three-dimensional model may be a surface mesh model. For example, FIG. 3B illustrates a three-dimensional tissue model 350 generated by a SLAM technique. The tissue model may have a coordinate frame $(X_M, Y_M, Z_M)$ that is registered to the image coordinate frame $X_I$, $Y_I$, $Z_I$. In other examples, the three-dimensional model may be a textured surface model. The SLAM technique may be performed intra-operatively, as the image capturing device moves within the patient anatomy. In other examples, a three-dimensional surface model may be generated pre-operatively using other imaging techniques.

Referring again to FIG. 1, if a determination is made at process 110 that no three-dimensional surface model is available, at a process 118, a path between the first and second marked points is rendered as a straight two-dimensional line between the marked points. With reference to FIG. 2, if no three-dimensional surface model is available, a straight line 208 may be generated between the surface points 204, 206. The line 208 appears to extend through the tissue 202 rather than across the surface. Any dimensions of the line 208 or measurements taken using the line 208 as a ruler may not accurately measure the surface-traversing distance between points 204 and 206. In some examples, the length of line 208 may be measured only in the X-Y plane and may not include a depth (Z-direction component). In some examples, the length of line may have a three-dimensional length but may be a straight line between the points 204, 206, without consideration of anatomical surfaces that extend between the marked points.

Referring again to FIG. 1, if a determination is made at a process 110 that a three-dimensional surface model is available, at a process 112 a perturbation may be made to the virtual camera to allow a clinician to view the surgical environment from a slightly changed angle. For example, the viewing angle or virtual camera tilt angle of the virtual camera may be tilted or changed slightly, as compared to the viewing angle of the live endoscopic imaging system. Thus, the virtual camera may view mixed-reality image (e.g., image frame 200), including the marked points 204, 206 and the tissue surface from a different viewpoint than the live endoscopic imaging system.

At a process, 114, a three-dimensional curvilinear segment may be generated between the marked points on the surface model. For example, and with reference to FIG. 3B, if a surface model 350 for the tissue 202 has been generated, the points 204, 206 may be located on the model 350, and a three-dimensional curvilinear segment 352 may be generated across the surface model between the points 204, 206. The dimensions and shape of the curvilinear segment 352 and any measurements taken using the line 210 may more accurately reflect the contoured shape of the tissue 202 and the surface-traversing distance between the points 204, 206 (as compared to the straight line 208).

Figure 3C:
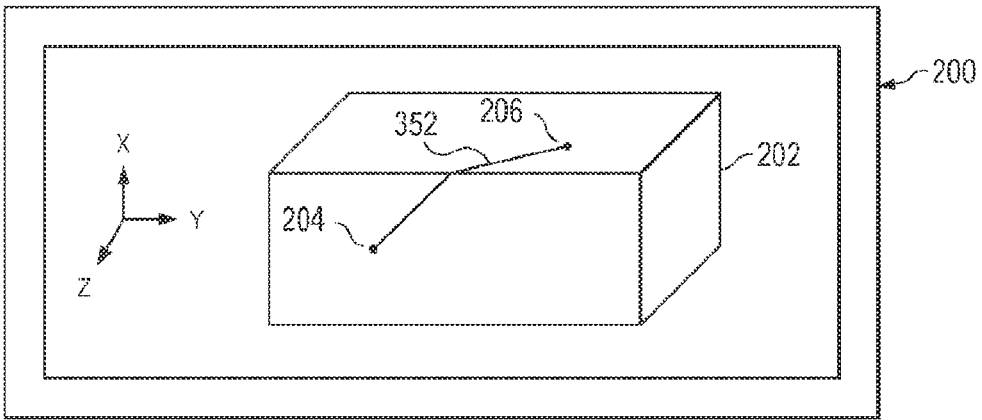
FIG. 3C illustrates the image of FIG. 2 modified to include curvilinear line segments that track tissue surfaces between the marked points, according to some embodiments.

At a process 116, the curvilinear segment may be added to the endoscopic image and used at process 108 to generate an updated mixed reality image frame. For example, and with reference to FIG. 3C, the three-dimensional endoscopic image 200 may be annotated to include the curvilinear line segment 352 traversing the surface of the tissue 202 between the points 204, 206. The curvilinear segment across the surface model allows for calculation of the surface distance which may be used, for example, to determine a correct amount of repair material, such as surface repair mesh or suture material, that may be needed. In some examples the curvilinear segment may allow for assessment of a pathology such as a hernia that is indicated by a bulging tissue. In some examples, multiple points may be indicated and used to create a multi-point line or polygon shape, the length or surface area of which may be measured.

In some examples, the surface model may be generated before the first and second marked points are placed. If, for example, a clinician would like to place a second marked point at a location that is not visible in the endoscopic camera field of view when the first marked point is placed, the projected curvilinear segment maybe progressively added to the surface model as the clinician pans the endoscopic camera to place the second marked point. The virtual camera may also or alternatively zoom out to display a three-dimensional view of the surgical environment that includes both the first and second marked points and the curvilinear segment connected the points. In some examples, if multiple points have been marked and multiple curvilinear segments have been generated in different locations in the anatomic environment, the virtual camera may generate a virtual view that encompasses all of the marked points and curvilinear segments so that the clinician may have an overview (e.g., a bird's eye view) of all the segments and the measurements associated with the segments. The overview image may be displayed in an adjacent display area or in a picture-in-picture display area throughout the clinical procedure. Thus, a clinician may avoid losing sight of generated segments.

Figure 4:
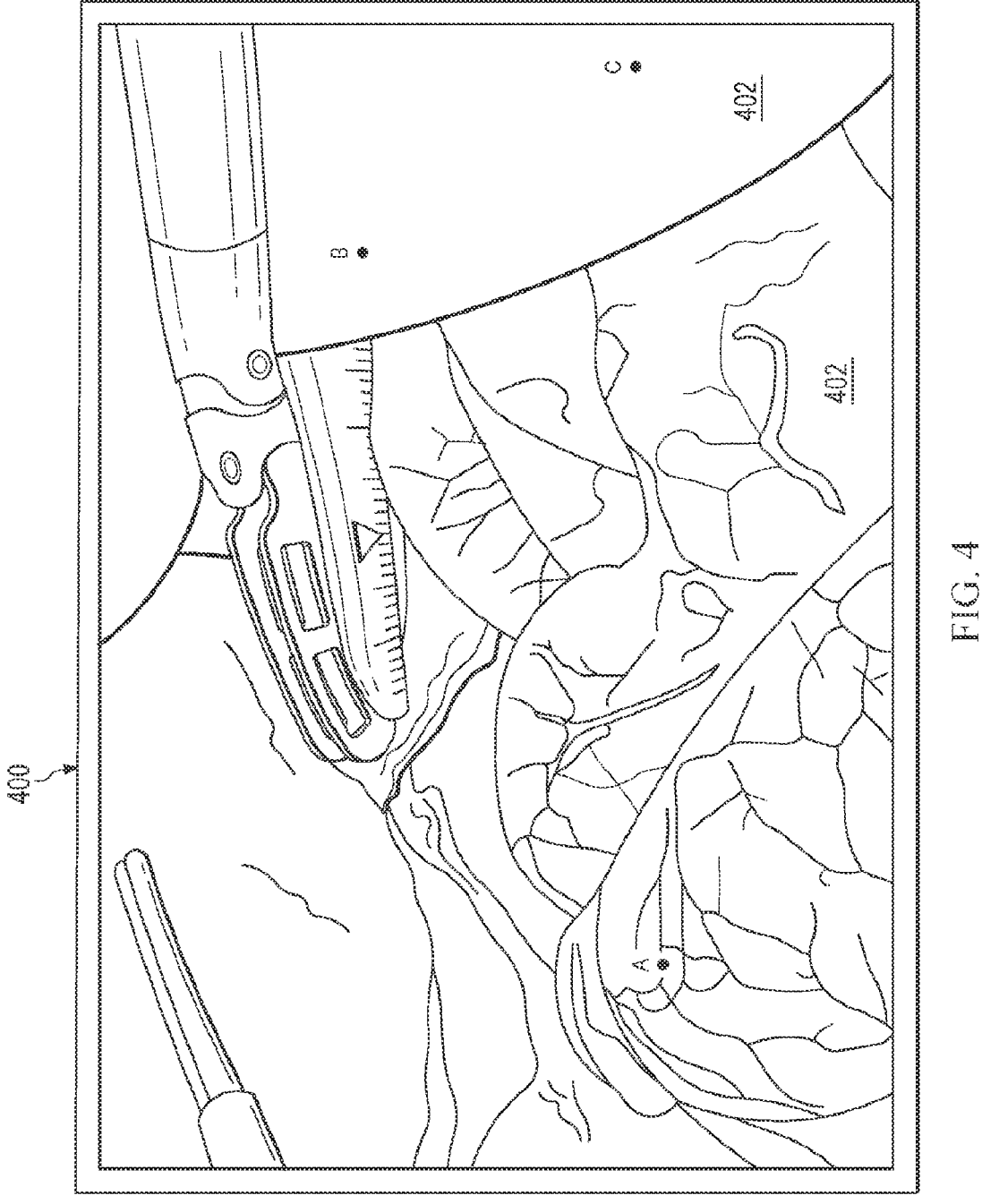
FIG. 4 is a three-dimensional endoscopic image with marked points on the surface of the imaged issue, according to some embodiments.
Figure 5:
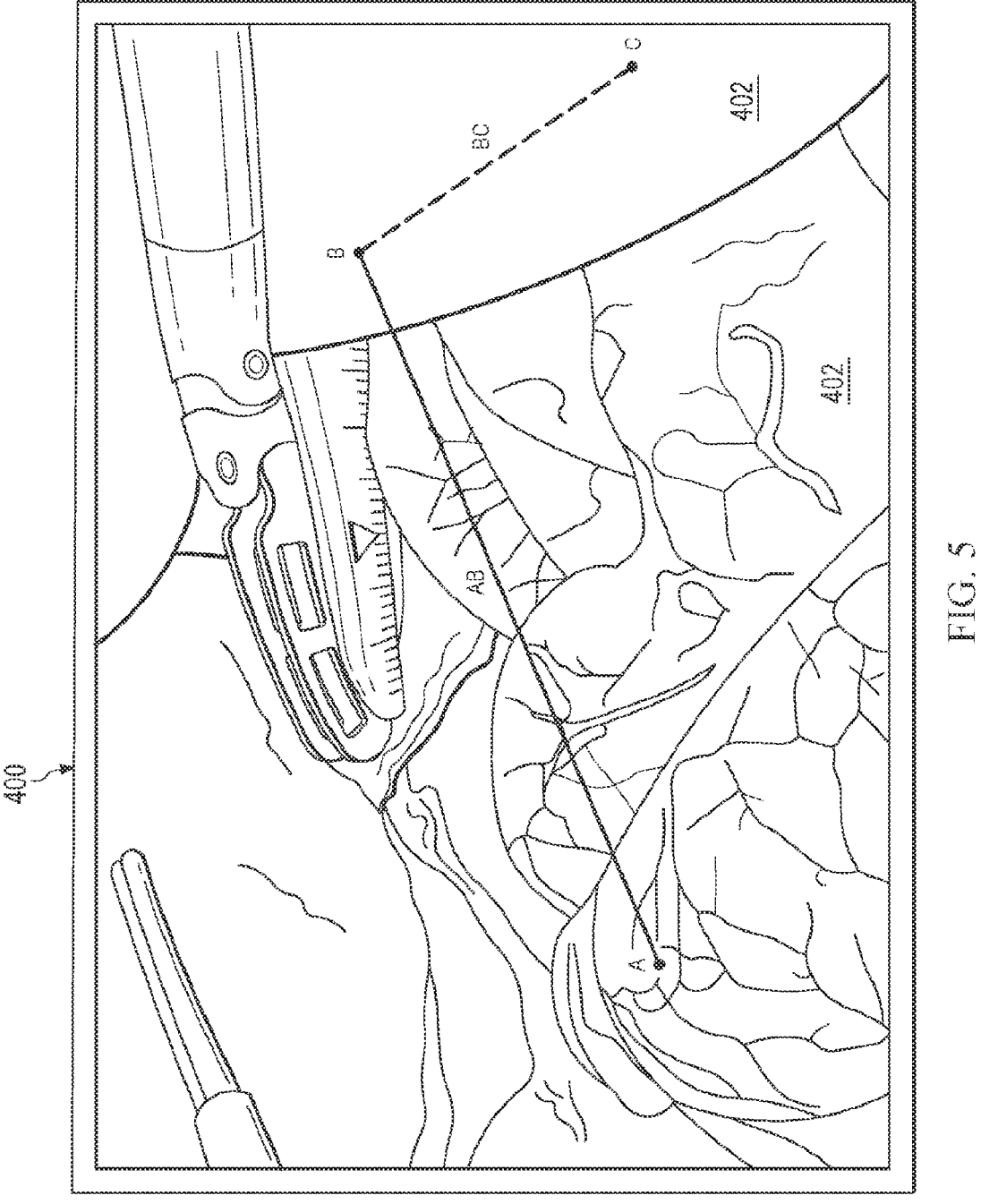
FIG. 5 is the endoscopic image of FIG. 4 with straight lines rendered between the marked points.
Figure 6:
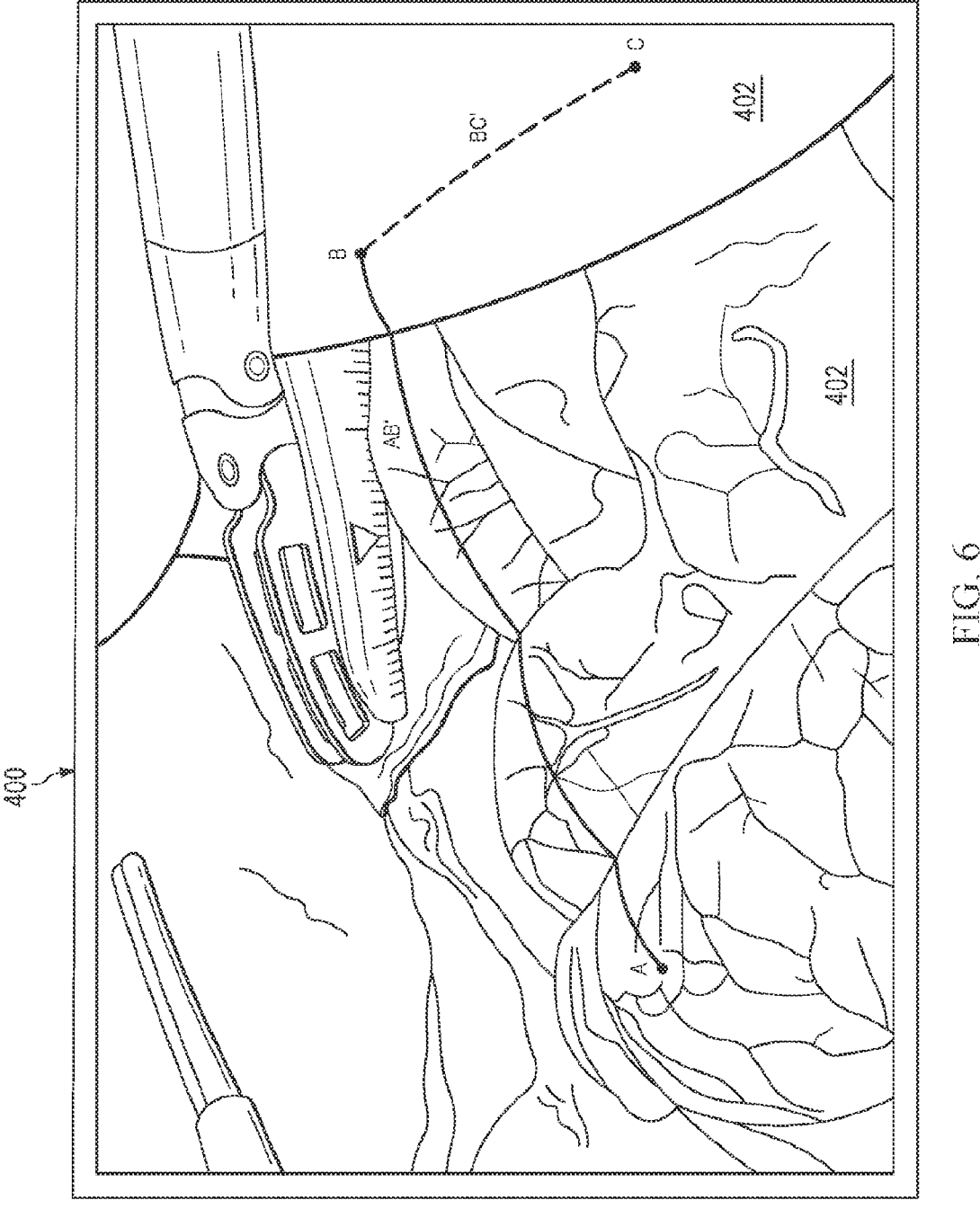
FIG. 6 is the endoscopic image of FIG. 5 with surface traversing lines rendered between the marked points.

FIG. 4 illustrates a stereo endoscopic image 400 of a surgical environment including tissue 402. As described in process 106 above, marked points A, B, and C may be received. If a surface model of the tissue 402 has not been generated, straight lines may be generated between the points according to process 118 and as shown in FIG. 5. For example, line segment AB may appear to float above float above the tissue, and the line segment BC may appear to extend through the tissue. If a surface model of the tissue 402 has been generated, for example a mesh surface model generated by a SLAM process, curvilinear lines may be generated between the points according to process 114 and as shown in FIG. 6. In FIG. 6, the curved lines AB' and BC' more accurately depict the contours of the tissue 402. The curved lines AB' and BC' traverse the surface of the tissue 402 and thus have a different length than the straight lines AB and BC of FIG. 5. The lines AB' and BC' may serve as a flexible ruler or tape measure to determine the distance between the marked points. The curved lines AB' and BC' may allow for more accurate measurements of the surface distance between the points A, B, C or of the undulating surface area between a plurality of points.

The systems and methods described herein may be implemented with a robotically-assisted medical system that includes an endoscopic imaging system, user input devices for identifying the surface points, and a display system for displaying the rendered endoscopic and mixed-reality images. FIG. 7 is a simplified diagram of a robotically-assisted medical system 700 that may be used with the systems and methods described herein. In some embodiments, system 700 may be suitable for use in therapeutic, diagnostic, and/or imaging procedures. While some embodiments are provided herein with respect to such procedures, any reference to medical or surgical instruments and medical or surgical methods is non-limiting. The systems, instruments, and methods described herein may be used for animals, human cadavers, animal cadavers, portions of human or animal anatomy, non-surgical diagnosis, as well as for industrial systems and general robotic, general teleoperational, or robotic medical systems. For example, the systems, instruments, and methods described herein may be used for non-medical purposes including industrial uses, general robotic uses, and manipulating non-tissue work pieces.

As shown in FIG. 7, system 700 generally includes a manipulator assembly 702. The manipulator assembly 702 is used to operate a medical instrument 703 (e.g., a surgical instrument) and medical instrument 704 (e.g., an image capturing device) in performing various procedures on a patient P. The manipulator assembly 702 may be teleoperated, non-teleoperated, or a hybrid teleoperated and non-teleoperated assembly with select degrees of freedom of motion that may be motorized and/or teleoperated and select degrees of freedom of motion that may be non-motorized and/or non-teleoperated. Manipulator assembly 702 is mounted to or located near an operating or surgical table T.

A user control system 706 allows an operator (e.g., a surgeon or other clinician as illustrated in FIG. 7) to view the interventional site and to control manipulator assembly 702. In some examples, the user control system 706 is a surgeon console, which is usually located in the same room as the operating or surgical table T, such as at the side of a table on which patient P is located. It is to be understood, however, that operator O can be located in a different room or a completely different building from patient P. That is, one or more user control systems 706 may be collocated with the manipulator assemblies 702, or the user control systems may be positioned in separate locations. Multiple user control systems allow more than one operator to control one or more robotically-assisted manipulator assemblies in various combinations.

User control system 706 generally includes one or more input devices for controlling manipulator assembly 702. The input devices may include any number of a variety of devices, such as joysticks, trackballs, data gloves, trigger-guns, hand-operated controllers, voice recognition devices, body motion or presence sensors, and/or the like. To provide operator O a strong sense of directly controlling medical instruments 703,704, the input devices may be provided with the same degrees of freedom as the associated medical instruments 703, 704. In this manner, the input devices provide operator O with telepresence and the perception that the input devices are integral with medical instruments 703, 704.

Manipulator assembly 702 supports medical instruments 703, 704 and may include a kinematic manipulator support structure of one or more non-servo controlled linkages (e.g., one or more links that may be manually positioned and locked in place), and/or one or more servo controlled linkages (e.g., one or more links that may be controlled in response to commands from a control system), and an instrument holder. Manipulator assembly 702 may optionally include a plurality of actuators or motors that drive inputs on medical instruments 703, 704 in response to commands from the control system (e.g., a control system 710). The actuators may optionally include drive systems that when coupled to medical instruments 703, 704 may advance medical instruments 703, 704 into a naturally or surgically created anatomic orifice. Other drive systems may move the distal end of medical instruments 703, 704 in multiple degrees of freedom, which may include three degrees of linear motion (e.g., linear motion along the X, Y, Z Cartesian axes) and three degrees of rotational motion (e.g., rotation about the X, Y, Z Cartesian axes). Additionally, the actuators can be used to actuate an articulable end effector of medical instrument 703 for grasping tissue in the jaws of a biopsy device and/or the like. Actuator position sensors such as resolvers, encoders, potentiometers, and other mechanisms may provide sensor data to system 700 describing the rotation and orientation of the motor shafts. This position sensor data may be used to determine motion of the objects manipulated by the actuators. The manipulator assembly 702 may position its held instruments 703, 704 so that a pivot point occurs at the instrument's entry aperture into the patient. The pivot point may be referred to as a remote center of manipulation. The manipulator assembly 702 may then manipulate its held instrument so that the instrument may be pivoted about the remote center of manipulation, inserted into and retracted out of the entry aperture, and rotated about its shaft axis.

System 700 also includes a display system 708 for displaying an image or representation of the surgical site and medical instrument 703 generated by the instrument 704. Display system 708 and user control system 706 may be oriented so operator O can control medical instruments 703, 704 and user control system 706 with the perception of telepresence. In some examples, the display system 708 may present images of a surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like.

System 700 also includes control system 710. Control system 710 includes at least one memory 714 and at least one computer processor 712 for effecting control between medical instruments 703, 704, user control system 706, and display system 708. Control system 710 also includes programmed instructions (e.g., a non-transitory machine-readable medium storing the instructions) to implement some or all of the methods described in accordance with aspects disclosed herein, including instructions for providing information to display system 708. While control system 710 is shown as a single block in the simplified schematic of FIG. 7, the system may include two or more data processing circuits with one portion of the processing optionally being performed on or adjacent to manipulator assembly 702, another portion of the processing being performed at user control system 706, and/or the like. The processors of control system 710 may execute instructions corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the robotic medical systems described herein. In one embodiment, control system 710 supports wireless communication protocols such as Bluetooth, IrDA, HomeRF, IEEE 802.11, DECT, and Wireless Telemetry.

Movement of a manipulator assembly 702 may be controlled by the control system 710 so that a shaft or intermediate portion of instruments mounted to the manipulator assemblies 702 are constrained to safe motions through minimally invasive surgical access sites or other apertures. Such motion may include, for example, axial insertion of a shaft through an aperture site, rotation of the shaft about its axis, and pivotal motion of the shaft about a pivot point adjacent the access site. In some cases, excessive lateral motion of the shaft that might otherwise tear the tissues adjacent the aperture or enlarge the access site inadvertently is inhibited. Some or all of such constraint on the motions of the manipulator assemblies 702 at the access sites may be imposed using mechanical manipulator joint linkages that inhibit improper motions or may in part or in full be imposed using data processing and control techniques. In some embodiments, control system 710 may receive force and/or torque feedback from medical instrument 704. Responsive to the feedback, control system 710 may transmit signals to user control system 706. In some examples, control system 710 may transmit signals instructing one or more actuators of manipulator assembly 702 to move medical instruments 703, 704.

In the description, specific details have been set forth describing some embodiments. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure.

Elements described in detail with reference to one embodiment, implementation, or application optionally may be included, whenever practical, in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions. Not all the illustrated processes may be performed in all embodiments of the disclosed methods. Additionally, one or more processes that are not expressly illustrated in may be included before, after, in between, or as part of the illustrated processes. In some embodiments, one or more of the processes may be performed by a control system or may be implemented, at least in part, in the form of executable code stored on non-transitory, tangible, machine-readable media that when run by one or more processors may cause the one or more processors to perform one or more of the processes.

Any alterations and further modifications to the described devices, instruments, methods, and any further application of the principles of the present disclosure are fully contemplated as would normally occur to one skilled in the art to which the disclosure relates. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The systems and methods described herein may be suited for imaging, any of a variety of anatomic systems, including the lung, colon, the intestines, the stomach, the liver, the kidneys and kidney calices, the brain, the heart, the circulatory system including vasculature, and/or the like. While some embodiments are provided herein with respect to medical procedures, any reference to medical or surgical instruments and medical or surgical methods is non-limiting. For example, the instruments, systems, and methods described herein may be used for non-medical purposes including industrial uses, general robotic uses, and sensing or manipulating non-tissue work pieces. Other example applications involve cosmetic improvements, imaging of human or animal anatomy, gathering data from human or animal anatomy, and training medical or non-medical personnel. Additional example applications include use for procedures on tissue removed from human or animal anatomies (without return to a human or animal anatomy) and performing procedures on human or animal cadavers. Further, these techniques can also be used for surgical and nonsurgical medical treatment or diagnosis procedures.

One or more elements in embodiments of this disclosure may be implemented in software to execute on a processor of a computer system such as control processing system.

When implemented in software, the elements of the embodiments of this disclosure may be code segments to perform various tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and/or magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc. Any of a wide variety of centralized or distributed data processing architectures may be employed. Programmed instructions may be implemented as a number of separate programs or subroutines, or they may be integrated into a number of other aspects of the systems described herein. In some examples, the control system may support wireless communication protocols such as Bluetooth, Infrared Data Association (IrDA), HomeRF, IEEE 802.11, Digital Enhanced Cordless Telecommunications (DECT), ultra-wideband (UWB), ZigBee, and Wireless Telemetry.

Note that the processes and displays presented might not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

This disclosure describes various instruments, portions of instruments, and anatomic structures in terms of their state in three-dimensional space. As used herein, the term position refers to the location of an object or a portion of an object in a three-dimensional space (e.g., three degrees of translational freedom along Cartesian x-, y-, and z-coordinates). As used herein, the term orientation refers to the rotational placement of an object or a portion of an object (e.g., in one or more degrees of rotational freedom such as roll, pitch, and/or yaw). As used herein, the term pose refers to the position of an object or a portion of an object in at least one degree of translational freedom and to the orientation of that object or portion of the object in at least one degree of rotational freedom (e.g., up to six total degrees of freedom). As used herein, the term shape refers to a set of poses, positions, or orientations measured along an object.

While certain illustrative embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A system comprising:

a processor; and a memory having computer readable instructions stored thereon, the computer readable instructions, when executed by the processor, cause the system to:

receive endoscope calibration data for an endoscope;

generate an endoscopic image;

receive first and second marked points in the endoscopic image;

generate a mixed reality image including the first and second marked points and the endoscopic image;

determine if a three-dimensional surface model has been generated; and if the three-dimensional surface model has been generated, generate a curvilinear segment contoured to the three-dimensional surface model between the first and second marked points, wherein the mixed reality image includes the contoured curvilinear segment.

2. The system of claim 1, wherein, the computer readable instructions, when executed by the processor, cause the system to: generate a virtual camera viewpoint different from an endoscope viewpoint and wherein the contoured curvilinear segment is visible in the virtual camera viewpoint from an angle different than the endoscopic viewpoint.

3. The system of claim 1, wherein if no surface model has been generated, a path between the first and second marked points is rendered as a straight line in the mixed reality image.

4. The system of claim 1, wherein the three-dimensional surface model includes a mesh model generated by simultaneous localization and mapping (SLAM).

5. The system of claim 4, wherein the SLAM model is generated intra-operatively while the endoscope is located within a patient anatomy.

6. The system of claim 1, wherein the computer readable instructions further cause the system to generate a virtual camera with the same calibration parameters as the endoscope.

7. The system of claim 6, wherein the computer readable instructions further cause the system to change virtual camera tilt angle of the virtual camera as compared to the endoscope.

8. The system of claim 1, wherein the computer readable instructions further cause the system to determine a length of the curvilinear segment.

9. The system of claim 8, wherein the computer readable instructions further cause the system to determine an amount of repair material for performing a procedure.

10. The system of claim 1, wherein the first and second marked points are part of a set of points used to determine length of a multi-point line or a surface area of a polygon shape.

11. A non-transitory machine-readable media storing instructions that, when run by one or more processors, cause the one or more processors to:

receive endoscope calibration data for an endoscope;

generate an endoscopic image;

receive first and second marked points in the endoscopic image;

generate a mixed reality image including the first and second marked points and the endoscopic image;

determine if a three-dimensional surface model has been generated; and if the three-dimensional surface model has been generated, generate a curvilinear segment contoured to the three-dimensional surface model between the first and second marked points, wherein the mixed reality image includes the contoured curvilinear segment.

12. The non-transitory machine-readable media of claim 11, when run by the one or more processors, generate a virtual camera viewpoint different from an endoscope viewpoint and wherein the contoured curvilinear segment is visible in the virtual camera viewpoint from an angle different than the endoscopic viewpoint.

13. The non-transitory machine-readable media of claim 11, wherein if no surface model has been generated, a path between the first and second marked points is rendered as a straight line in the mixed reality image.

14. The non-transitory machine-readable media of claim 11, wherein the three-dimensional surface model includes a mesh model generated by simultaneous localization and mapping (SLAM).

15. The non-transitory machine-readable media of claim 14, wherein the SLAM model is generated intra-operatively while the endoscope is located within a patient anatomy.

16. The non-transitory machine-readable media of claim 11, when run by the one or more processors, generate a virtual camera with the same calibration parameters as the endoscope.

17. The non-transitory machine-readable media of claim 16, when run by one or more processors, change a virtual camera tilt angle of the virtual camera as compared to the endoscope.

18. The non-transitory machine-readable media of claim 11, when run by one or more processors, determine a surface distance based on a length of the curvilinear segment.

19. The non-transitory machine-readable media of claim 18, when run by the one or more processors, determine an amount of repair material for performing a procedure.

20. The non-transitory machine-readable media of claim 11, wherein the first and second points are part of a set of points used to determine length of a multi-point line or a surface area of a polygon shape.

* * * * *